United States Patent [19]
Lasser et al.

[11] Patent Number: 5,940,425
[45] Date of Patent: Aug. 17, 1999

[54] LASER ARRANGEMENT HAVING AN AXIALLY OPTICALLY PUMPED LASER

[75] Inventors: Theo Lasser, Oberkochen; Herbert Gross; Robert Maag, both of Aalen, all of Germany

[73] Assignee: Carl-Zeiss-Stiftung, Heidenheim/Brenz, Germany

[21] Appl. No.: 08/790,593

[22] Filed: Jan. 29, 1997

Related U.S. Application Data

[63] Continuation of application No. 08/355,165, Dec. 8, 1994, abandoned.

[30] Foreign Application Priority Data

Apr. 30, 1994 [DE] Germany ............................ 44 15 269

[51] Int. Cl.⁶ ..................................................... H01S 3/093
[52] U.S. Cl. ................................. 372/72; 372/6; 372/69
[58] Field of Search ................................. 372/72, 6, 62, 372/70

[56] References Cited

U.S. PATENT DOCUMENTS

| | | |
|---|---|---|
| 4,383,318 | 5/1983 | Barry et al. ................................. 372/6 |
| 4,433,238 | 2/1984 | Adolfsson et al. ...................... 250/227 |
| 4,627,068 | 12/1986 | Johnson et al. ............................. 372/6 |
| 4,665,529 | 5/1987 | Baer et al. . |
| 4,723,257 | 2/1988 | Baer et al. . |
| 4,780,877 | 10/1988 | Snitzer ....................................... 372/71 |
| 4,794,615 | 12/1988 | Berger et al. .............................. 372/71 |
| 4,808,789 | 2/1989 | Muncheryan . |
| 4,879,722 | 11/1989 | Dixon et al. ............................... 372/21 |
| 4,917,486 | 4/1990 | Raven et al. ............................. 359/435 |
| 4,962,995 | 10/1990 | Andrews et al. ............................ 372/6 |
| 4,979,180 | 12/1990 | Muncheryan .............................. 372/75 |
| 5,084,880 | 1/1992 | Esterowitz et al. ......................... 372/6 |
| 5,107,516 | 4/1992 | Dressel et al. ............................. 372/69 |
| 5,123,845 | 6/1992 | Vassiliadis et al. . |
| 5,157,683 | 10/1992 | Millar et al. ................................. 372/6 |
| 5,187,759 | 2/1993 | DiGiovanni et al. ........................ 372/6 |
| 5,198,926 | 3/1993 | Sheinis et al. . |
| 5,214,664 | 5/1993 | Paoli . |
| 5,258,989 | 11/1993 | Raven ......................................... 372/6 |
| 5,323,409 | 6/1994 | Laskoskie et al. .......................... 372/6 |
| 5,392,308 | 2/1995 | Welch et al. .............................. 372/92 |
| 5,396,506 | 3/1995 | Ball ............................................. 372/6 |
| 5,434,880 | 7/1995 | Burrows et al. .......................... 372/69 |

FOREIGN PATENT DOCUMENTS 2190784 11/1987 United Kingdom .

*Primary Examiner*—Leon Scott, Jr.
*Attorney, Agent, or Firm*—Walter Ottesen

[57] ABSTRACT

An axially optically pumped laser 11 is penetrated coaxially by a target beam $\lambda_2$. This penetration of the pumped laser occurs via light conductor 2 by means of laser diode 31. The pumped laser 11 can be an erbium—YAG laser. For this purpose, the dispersion, diffraction and reflection of an incoupling optic 12, of laser 11 and a focusing device 13 are suitably matched to each other in order that the pump light $\lambda_3$, work beam $\lambda_1$ and target beam $\lambda_2$ are suitably guided and are suitable for small diameters. The laser arrangement is suitable as a medical device for ears, nose and throat and eyes and can be utilized with an endoscope.

20 Claims, 2 Drawing Sheets

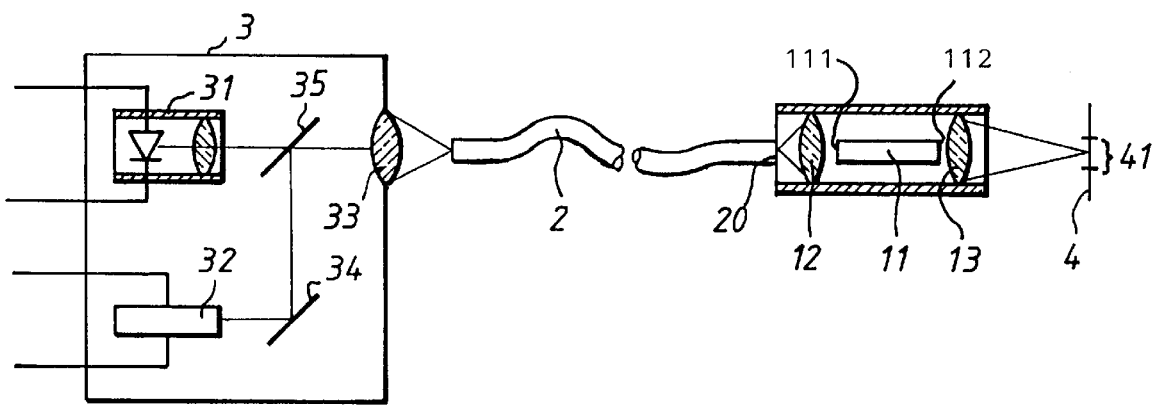
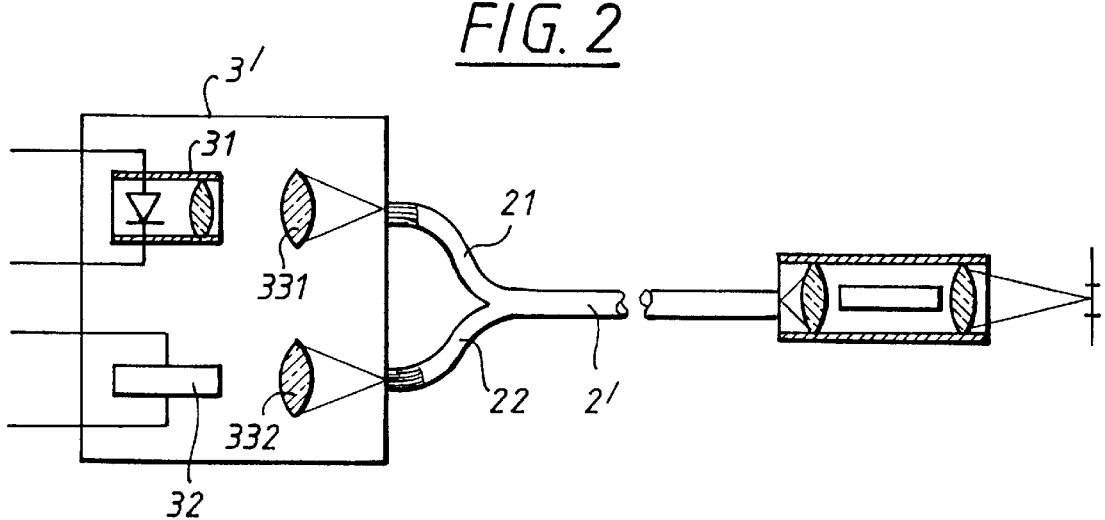
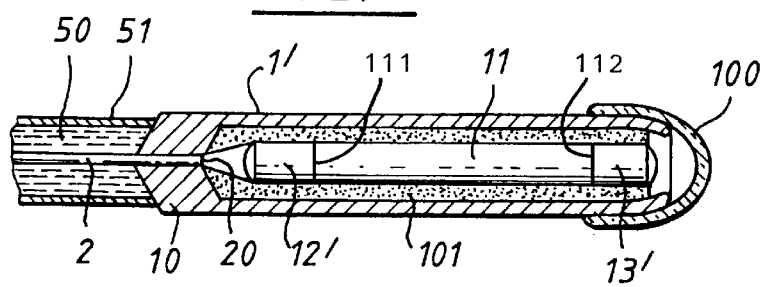

LASER ARRANGEMENT HAVING AN AXIALLY OPTICALLY PUMPED LASER

This is a continuation of application Ser. No. 08/355,165, filed on Dec. 8, 1994 now abandoned.

FIELD OF THE INVENTION

The invention relates to a laser arrangement having an axially optically pumped laser of a specific wavelength and having a focusing device. With the focusing device, the energy density of the exiting laser beam is at a maximum at a specific location.

BACKGROUND OF THE INVENTION

U.S. Pat. Nos. 4,723,257 and 4,665,529 disclose a solid-state laser pumped at one end by means of a laser diode array via a light-conducting fiber. The solid-state laser includes a focusing lens for the pump light. The laser medium is Nd—YAG or the like. For laser rod dimensions of 3 mm in diameter and 5 mm in length, the complete laser head, including a frequency doubler crystal, has a diameter of approximately 1 cm and a length of approximately 8.4 cm. A reduction in size of 32% to 50% is, however, indicated as being possible. A pilot beam is not provided.

U.S. Pat. No. 4,808,789 discloses a laser instrument suitable for surgery. The laser instrument includes a diode pumped Nd—YAG laser or the like wherein the laser beam is conducted to a handheld stylus via light-conducting fibers. The handheld stylus has a frequency doubler crystal and a zoom objective for focusing. A gas flow can exit from the conically-shaped end of the handheld stylus coaxially to the laser beam. An erbium laser completely integrated into a handheld stylus is also described. The erbium laser (FIG. 2) includes an axially arranged laser diode array as the pump source and is without optical fibers. The arrangement is intended to be compact but specific dimensions are not provided. The entire laser arrangement including battery is intended to be held in the housing shown; however, it cannot have a diameter of only a few millimeters.

U.S. Pat. No. 5,198,926 discloses a surgical laser device having a visible target beam and an IR-power beam having a wavelength of 3 μm or more. The beams are focused via an achromatic objective onto a common point. The achromatic objective is made of suitable material. Superposition takes place with a dichroic mirror.

U.S. Pat. No. 5,214,664 discloses a coaxially emitting multiple wavelength solid-state laser. The solid-state laser here includes a laser diode of the Ga—As type. The wavelengths of 778 nm and 843 nm are mentioned as exemplary. However, it is not possible to derive a simultaneous emission in the visible and the mid IR-range from the disclosure of this patent.

U.S. Pat. No. 4,917,486 discloses a photocoagulator based on a slit lamp. The photocoagulator has an IR-laser diode and visible laser diode for the target beam which is superposed by means of a dichroic mirror.

Although light conductors for the wavelength of erbium lasers (approximately 3 μm) are obtainable (ZBLAN-fibers), they are, however, problematical because they can be toxic (material: fluoride), expensive and do not sustain much use.

U.S. Pat. No. 5,123,845 discloses a dental laser arrangement having a solid-state laser which is pumped laterally via flash lamps. For example, the solid-state laser can be an erbium laser which is coaxially transilluminated by a He—Ne-target laser which is transmitted to a handheld member for treatment via a light conductor transmitting unit. This configuration can in no way be compact and the difficulty of the light conductor with respect to the wavelength of the erbium laser in not eliminated.

SUMMARY OF THE INVENTION

It is an object of the invention to provide a laser arrangement which provides a power beam and a target beam and is of a very compact configuration. The laser arrangement according to the invention has especially a small diameter. The laser arrangement is intended to be suitable as a laser applicator without additional parts even for locations which are difficult to access such as for medical treatment in cavities of the body and the like.

The laser arrangement of the invention includes: an axially optically pumped laser having a specific first wavelength ($\lambda_1$) and defining an optical axis; the laser having an input end face and an output end face from which laser light having the first wavelength ($\lambda_1$) passes as a first laser light beam down the axis; a focusing device mounted on the axis downstream of the output end face for focusing the first laser light beam to a predetermined location where the energy density of the first laser light beam is a maximum; and, laser light source means for generating a second laser light beam of a second wavelength ($\lambda_2$) traveling along the optical axis and through the laser for generating a concentrated light spot at the predetermined location.

In this laser arrangement, a second laser beam of a second wavelength enters the laser coaxially with the pumped light and generates a concentrated light spot at the location of maximum energy density of the laser.

It was found that it is possible to match the reflecting and refracting properties of the required optical elements in such a manner that the light of the first wavelength of the work beam, of the second wavelength of the target beam and of the third wavelength of the pump light is guided simultaneously in a predetermined way.

It is advantageous that: the cross section of the first laser beam at the location of maximum energy density is less or equal to the cross section of the second laser beam in the concentrated light spot (the laser action is then always limited within the illuminated target area); the second wavelength of the second laser beam lies in the visible spectrum and is therefore a proper target laser; the specific wavelength of the laser lies in the infrared spectral range; the pump light has a third wavelength in the near infrared region; the laser is a solid-state laser; the laser is an erbium laser; the pump light and the second laser beam are guided to the laser via light conductors because this makes possible a very narrow and flexible embodiment; or, different light conductors are provided for the pump light and the second laser beam with the light conductors being bundled in common. The light conductors can then be individually optimized for the various wavelengths and the incoupling is possible without superposing elements. The above-mentioned features are advantageous individually and in various combinations.

It is especially advantageous to provide a collimating optic which approximately collimates the pump light and the second laser beam in the region of the laser. For a laser resonator which emits a parallel laser beam of the specific wavelength, the common bundling with the target beam (second laser beam) is easily possible with optics of lower dispersion.

Alternatively, it is purposeful to provide a focusing optic which concentrates the pump light and the second laser beam in the region of the laser. Accordingly, and if required, a higher efficiency of the pumping is made possible. However, special measures for simultaneous focusing of target beam and work beam are necessary, for example, a diffractive optic.

The laser arrangement becomes compact in diameter when the cross sections of the pump light, work beam and target beam do not deviate more than 30% from each other in a component region of the laser rod so that the material for guiding light and for laser beam generation is optimally utilized.

Greater freedom in the configuration of the individual beam paths is provided when the focusing device contains the collimator optic or the focusing optic contains one or more diffractive elements.

For simple manufacture, it is inter alia preferable that: the laser has plane parallel laser resonator mirrors; one or two resonator mirrors are mounted directly on the laser solid body; or, the focusing device, the collimator optic or the focusing optic is connected directly to a resonator mirror.

In a preferred embodiment, the diameter of all light beams between the light conductor exit and the location of maximum energy density is less than 1.5 mm whereby the total laser arrangement can be configured to be extremely narrow.

According to another feature of the invention, the first laser beam (the work laser) is not conducted through a light wave conductor. This embodiment is especially advantageous at wavelengths in the mid-infrared range (for example, with an erbium laser) because then no material problems occur for suitable light conductors.

The laser arrangement according to the invention is suitable especially as a medical treatment apparatus for which the target laser is a necessary prerequisite and the compactness ensures a high movability and accessibility to the treatment locations. The medical treatment apparatus is especially suitable for treating the eyes, ears, the nose and throat area, the teeth as well as in combination with an endoscope. It can also be configured as a photocoagulator or as a laser ablation apparatus.

BRIEF DESCRIPTION OF THE DRAWINGS

The invention will now be described with reference to the drawings wherein:

FIG. 1 is a schematic of the overall laser arrangement according to the invention;

FIG. 2 corresponds to FIG. 1 but shows an alternate pump light supply;

FIG. 3 is a schematic of a laser treating device;

DESCRIPTION OF THE PREFERRED EMBODIMENTS OF THE INVENTION

Figure 4:
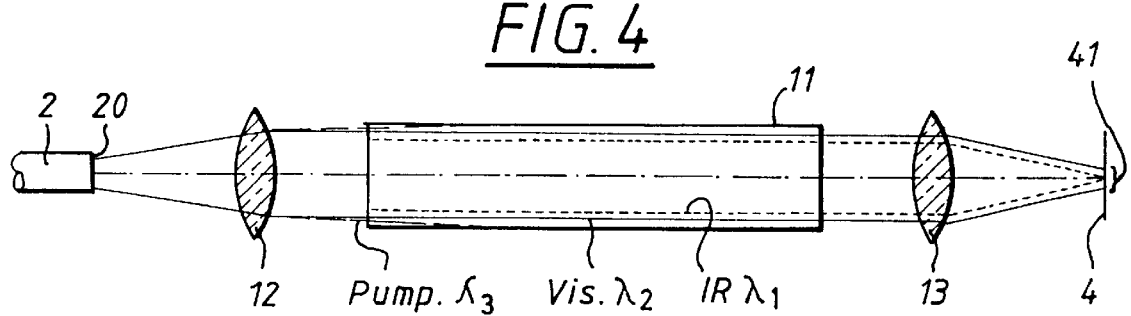
FIG. 4 is a schematic showing the beam paths for the three wavelengths.

FIG. 1 shows a laser arrangement 1 having a laser 11 which here is an erbium YAG laser rod having dielectric resonator mirrors (111, 112) applied directly thereto, a collimator or focusing optic 12 and a focusing device 13. The focusing optic 12 is configured as a single lens and the focusing device 13 is configured as a sapphire lens which is transparent simultaneously for mid-infrared light and visible light. An object 4 with the concentrated light spot 41 is arranged in the region of the waist of the focusing device 13.

A light conductor 2 conducts the light of light source 3 axially to the laser arrangement 1. The light conductor 2 has an exit face 20 and can also be configured as a light-conducting fiber bundle.

The light source 3 includes a laser diode 31 having a collimator optic such as a laser diode array having a power in the order of magnitude of 1 Watt. The laser diode array is provided for generating the pump light at the third wavelength $\lambda_3$ in the near infrared and is suitable for pumping the erbium laser 11. A VIS-laser 32 has visible light of the second wavelength $\lambda_2$ for the target beam and can, for example, be a He—Ne-laser having a power in the milliwatt range or the laser 32 can be an appropriately configured laser diode. The two beams of wavelengths $\lambda_2$ and $\lambda_3$ are superposed by the mirror 34 and the dichroic mirror 35 and are coupled into the light conductor by lens 33.

FIG. 2 shows an alternate embodiment of a light source 3' and a light conductor 2'. The light conductor 2' consists of several fibers which are illuminated in two bundles (21, 22) separately with light of wavelength $\lambda_3$ and $\lambda_2$, respectively, by the laser diode 31 having lens 331 and by VIS-laser 32 having lens 332. The fibers of the two bundles (21, 22) can be randomly or uniformly distributed in light conductor 2' or can, for example, appear as concentric rings at the exit face 20.

FIG. 3 shows a medical treatment apparatus 1' having laser 11 and resonating mirrors (111, 112). Planar convex lenses (12', 13') are mounted directly on the resonator mirrors (111, 112). The assembly of laser 11 and lenses (12', 13') is attached with a layer of adhesive or filling paste 101 in the housing. The housing 10 is made of metal, ceramic or plastic and holds the light conductor 2 with its end face 20 in the correct position to lens 12'. An adjustment during the assembly is possible in that an optical element and its holder are adjusted in position with the aid of an auxiliary device and then fixed in position utilizing epoxy or some other curing substance. This assembly technique is described in U.S. Pat. No. 4,805,993 incorporated herein by reference.

The materials of the filling paste 101 and of the housing 10 should be selected so that they are excellent heat conductors to conduct away the waste heat of the laser 11. The filling paste 101 is applied as thin as possible in order to obtain a minimal diameter of the overall treating device 1'. A metallic solder is especially suitable as a filling paste 101. This metallic solder is also especially suitable to provide an effective thermal connection during the soldering. The light conductor 2 is surrounded by a sleeve 51 in which a fluid 50 can be provided as a coolant. The transparent protective jacket 100 can be exchanged and can be sterilized and is important for use in medical applications. The protective jacket can enclose the entire treating device 1' as required.

The means disclosed in U.S. Pat. No. 4,665,529 are, for example, also useable for assembly and adjustment. U.S. Pat. No. 4,665,529 is incorporated herein by reference.

According to the invention, the beam paths of the pump beam $\lambda_3$, work beam $\lambda_1$ and target beam $\lambda_2$ are arranged coaxially in the laser arrangement (1, 1') and the optical elements (11, 12, 13) are transilluminated by at least two different wavelengths ($\lambda_1$, $\lambda_2$, $\lambda_3$). The dispersion must be taken into account for the diffraction at the lenses (12, 13) and, if required, at the laser rod 11. Dichroic dielectric mirrors (111, 112) on the laser 11 permit, with known means, the following: unimpeded pass-through of the target beam at $\lambda_2$; high reflection for the resonator assembly at $\lambda_1$ with suitable outcoupling; the inlet of pump light at $\lambda_3$; and, the back reflection of $\lambda_3$ at the exit end resonator mirror 112 for short lengths of the laser rod.

Figure 5:
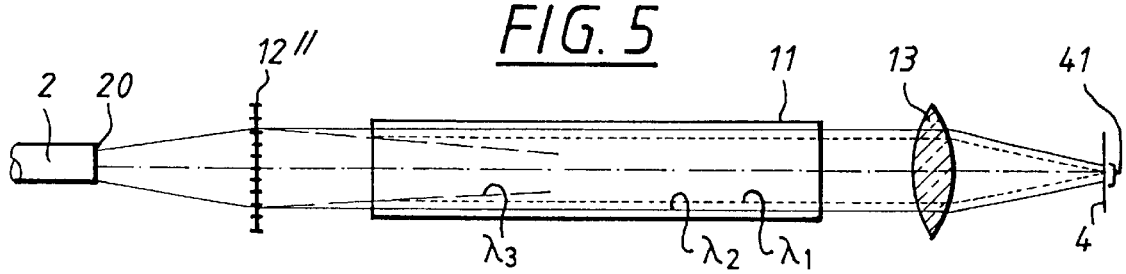
FIG. 5 is another embodiment for the beam paths wherein a diffractive element is provided.
Figure 6:
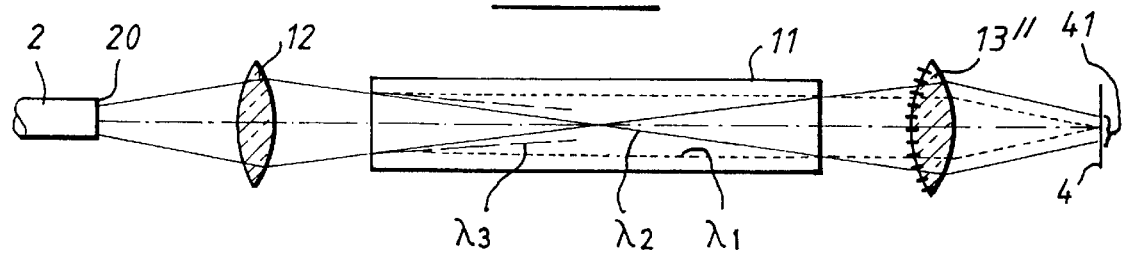
FIG. 6 is a further embodiment for the beam paths.

FIGS. 4 to 6 show the laser arrangement according to the invention with various suitable beam geometries.

FIG. 4 shows the light conductor 2 with its exit face 20 which has the same aperture for the target light $\lambda_2$ (solid line) and the pump light $\lambda_3$ (dotted line). The lens 12 is configured as a collimator and therefore makes the rays of the target beam $\lambda_2$ parallel and the pump light $\lambda_3$ lying in the near infrared range is made slightly divergent by the dispersion. This can be accepted and pumping remains adequately effective. The laser beam $\lambda_1$ (dash-dotted line) of the laser 11 is generated approximately diffraction limited parallel because of the plane parallel resonator mirrors. The infrared transparent focusing device (sapphire lens) 13 refracts the parallel work beam $\lambda_1$ and target beam $\lambda_2$ differently because of the dispersion effect so that a concentrated light spot 31 of the target laser beam $\lambda_2$ is generated on an object 4 at a location where also the region of maximum energy density of the work beam $\lambda_1$ is located. The above-mentioned dispersion effect is considerable because of the considerably different wavelengths. As a rule, it is also desired and suitable for medical applications, that this region is somewhat larger than the region encompassed by the work beam $\lambda_1$.

An embodiment of FIGS. 1 and 4 has the following data:

| | | |
|---|---|---|
| laser diode 31 | series SDL 63XX | wavelength $\lambda_3$= 960 nm |
| laser 32 | laser diode | wavelength $\lambda_2$= 670 nm |
| optical fiber 2 | diameter 160 μm | numerical aperture 0.1 |
| spacing of end face (20) to lens 12 | 3.4 mm | |
| first face of 12 | planar | |
| thickness of 12 | 2.5 mm | |
| second lens radius of 12 | −2.59 mm convex | |
| focal length of 12 | 5 mm | |
| diameter of 12 | 1 mm | |
| material of 12 | Glass Schott BK7 | |
| dispersion: | at $\lambda_3$ n = 1.508 | |
| | at $\lambda_2$ n = 1.514 | |
| distance of 12 to 11 | 4 mm (up to 20 mm) | |
| laser 11 | Er-YAG-crystal having approximately 50% Er-doping | |
| dispersion: | at $\lambda_1$ n = 1.787 | |
| | at $\lambda_2$ n = 1.821 | |
| | at $\lambda_3$ n = 1.831 | |
| length 10 mm, diameter 1 mm, plane-parallel end faces. | | |
| Pump-light end coating HR for $\lambda_1$, AR for $\lambda_2$, $\lambda_3$. | | |
| Output end coating reflective (specific for application) | | |
| (95 to 99.7%) for $\lambda_1$, | | |
| HR for $\lambda_3$, AR for $\lambda_2$. | | |
| Laser wavelength $\lambda_1$ = 2.94 μm. | | |

Spacing to the outcoupling lens 13 (focusing device) 2 mm (variable 0 to 20 mm),

| | |
|---|---|
| first radius of out-coupling lens 13 | 7.7 mm convex |
| thickness of 13 | 2.0 mm |
| second surface of 13 | planar |
| focal length of 13 | 10 mm |
| diameter of 13 | 1 mm |
| material of 13 | sapphire |
| Dispersion: at $\lambda_1$ n = 1.721, at $\lambda_2$ n = 1.765. | |

Working distance between lens 13 and object 4: 10 mm.

When the lens 12 is exactly adjusted to collimation of the pump light at $\lambda_3$, then the target beam $\lambda_2$ is slightly defocused (by 0.75 mm) on the object 4 because of the dispersion of the components (11, 12, 13) and the light spot 41 has a diameter of approximately 0.33 mm. The diameter of the work beam $\lambda_1$ amounts at this location to approximately 0.10 mm. This is a dimension of the two light spots of $\lambda_1$ and $\lambda_2$ which is suitable in practice for medical laser treating devices.

The pump light $\lambda_3$ does not have to enter into the laser 11 exactly collimated. In this case, the spacing between the light conductor end 20 and the collimating lens 12 can also be so adjusted that the target beam $\lambda_2$ is sharply adjusted on the object 4.

The work beam $\lambda_1$ (2.94 μm) has a significantly greater depth of focus (0.5 mm) than the target beam $\lambda_2$ (670 nm) at only 0.11 mm because of the greatly different wavelengths. The relative focus position of $\lambda_1$ and $\lambda_2$ is therefore not critical in the context of depth of focus.

In the arrangement shown, the beam trace of the pump light $\lambda_3$ in the Er—YAG laser rod 11 is almost parallel. Accordingly, there is no concentration of the pump light $\lambda_3$ and, depending on the precise configuration, there can therefore be a drop below the threshold value power for the laser excitation. Then, a focusing of the pump light $\lambda_3$ is required. FIGS. 5 and 6 show possible configurations for this purpose.

FIG. 5 corresponds to FIG. 4 except that the lens 12 is replaced by a diffractive element 12". The diffractive element 12" focuses the pump beam $\lambda_3$ in the laser 11 but collimates the target beam $\lambda_2$. Such diffractive elements 12" are known with several superposed grating structures.

The desired focusing of the pump light $\lambda_3$ is obtained without anything being changed in the beam path at $\lambda_1$ and $\lambda_2$ with respect to FIG. 4.

In FIG. 6, the lens 12 focuses the pump light $\lambda_3$ and the target beam $\lambda_2$ into the laser 11. This is achieved by appropriately selecting the focal length and the spacing to the exit face 20 of the light conductor 2.

The focusing device 13" must then focus the divergent target beam $\lambda_2$ and the parallel work beam $\lambda_1$ at the same time on the object 4. This can be achieved with adequate approximation in many cases utilizing the dispersion of one or more lenses, the relationships described above of the depth of focus at $\lambda_1$ and $\lambda_2$ and the desired diameters of the light spots 41. A diffractive element, however, can be also used here as described in FIG. 5 or a diffractive element 13" shown here combined with a lens can be used.

Figure 7:
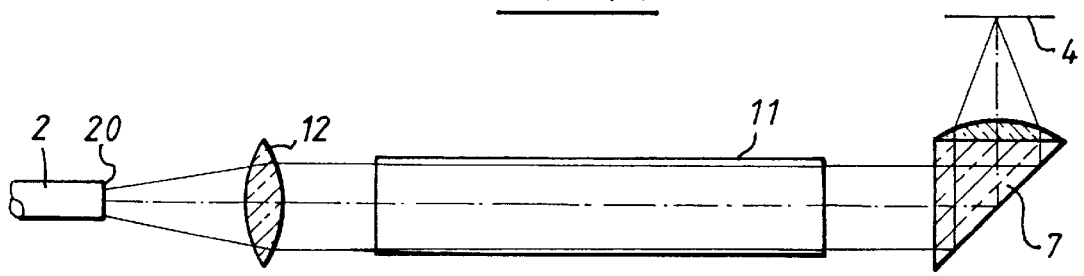
FIG. 7 shows an embodiment with a deflecting prism.

Especially in medical laser treating devices, an angled, for example, radial direction of the work beam $\lambda_1$ is needed. This direction is angled with respect to the longitudinal direction of the instrument. FIG. 7 shows one such embodiment of the arrangement of the invention.

The arrangement corresponds to FIGS. 1 and 4 and is the same except that the lens 13 is replaced by a prism 7 having a lens surface which simultaneously effects the desired deflection and the focusing.

It is understood that the foregoing description is that of the preferred embodiments of the invention and that various changes and modifications may be made thereto without departing from the spirit and scope of the invention as defined in the appended claims.

What is claimed is:

1. A laser arrangement comprising:

a pump light source generating a pump light;

a first laser having a specific first wavelength ($\lambda_1$) and defining an optical axis;

said first laser having an input end face for axially receiving said pump light from said pump light source and for being pumped by said pump light;

said first laser having an output end face from which a first laser light beam having said first wavelength ($\lambda_1$) passes as a first laser light beam down said axis and said first laser light beam having an energy density;

a focusing device mounted on said axis downstream of said output end face of said first laser for focusing said first laser light beam so as to cause said energy density of said first laser light beam to be a maximum at a predetermined location;

a second laser generating a second laser light beam of a second wavelength ($\lambda_2$) traveling along said optical axis and through said axially optically pumped first laser and said focusing device generating a concentrated light spot at said predetermined location; and, a light conductor common to both said pump light source and said second laser for conducting said pump light and the light of said second laser light beam into said first laser along said axis thereof.

2. The laser arrangement of claim 1, wherein said first laser light beam has a first cross section at said predetermined location; said second laser light beam has a second cross section at said concentrated light spot; and, said first cross section is equal to or less than said second cross section.

3. The laser arrangement of claim 1, wherein said second wavelength ($\lambda_2$) lies in a spectrum of visible light.

4. The laser arrangement of claim 1, wherein said first wavelength ($\lambda_1$) lies in a spectral range of infrared light.

5. The laser arrangement of claim 1, wherein said pump light has a third wavelength ($\lambda_3$) lying in a spectral range of near infrared light.

6. The laser arrangement of claim 1, said first laser being a solid-state laser having a laser rod.

7. The laser arrangement of claim 6, said solid-state laser being an erbium laser.

8. The laser arrangement of claim 6, said solid-state laser including a laser rod; and, said arrangement further comprising at least one resonator mirror mounted directly on said laser rod.

9. The laser arrangement of claim 1, said light conductor having a Y configuration with first and second legs and a third leg connected to said first and second legs; said first and second legs being optically connected to said pump light source and said second laser, respectively; and, said first and second legs having respective sets of optical fibers commonly bundled in said third leg and extending from said first and second legs; and, said third leg being optically connected to said first laser.

10. The laser arrangement of claim 1, further comprising a collimator approximately collimating the light beam of said second laser and said pump light of said pump light source in the region of said first laser.

11. The laser arrangement of claim 10, said collimator including at least one diffractive element.

12. The laser arrangement of claim 10, further comprising one resonator mirror mounted directly on said collimator.

13. The laser arrangement of claim 1, further comprising a focusing arrangement focusing said first laser light beam and said second laser light beam at said predetermined location.

14. The laser arrangement of claim 13, said focusing arrangement including at least one diffractive element.

15. The laser arrangement of claim 13, further comprising one resonator mirror mounted directly on said focusing arrangement.

16. The laser arrangement of claim 1, wherein:

said first laser includes a laser rod defining said input and output end faces;

said first laser light beam, said second laser light beam and said pump light having respective cross sections which do not depart from each other by more than 30% in at least a part of said laser rod of said first laser.

17. The laser arrangement of claim 1, said first laser having first and second plane parallel resonator mirrors.

18. The laser arrangement of claim 1, said light conductor having an outlet upstream of said first laser; said first laser light beam having a first diameter; said second laser light beam having a second diameter; and, said pump light having a third diameter; and, said diameters each being less than 1.5 mm between said outlet and said predetermined location.

19. The laser arrangement of claim 1, said input end face and said predetermined location conjointly defining a space therebetween devoid of a light conducting fiber.

20. The laser arrangement of claim 1, further comprising one resonator mirror mounted directly on said focusing device.

* * * * *